US005519020A

United States Patent [19]
Smith et al.

[11] Patent Number: 5,519,020
[45] Date of Patent: May 21, 1996

[54] POLYMERIC WOUND HEALING ACCELERATORS

[75] Inventors: Daniel J. Smith, Stow; Sharon Pulfer, Clinton; Mohammad Shabani, Akron, all of Ohio

[73] Assignee: The University of Akron, Akron, Ohio

[21] Appl. No.: 330,596

[22] Filed: Oct. 28, 1994

[51] Int. Cl.$^6$ ..................................................... A61K 31/54
[52] U.S. Cl. .......................... 424/718; 514/54; 424/444; 424/499; 424/488; 424/500
[58] Field of Search ........................................ 514/227, 54

[56] References Cited

U.S. PATENT DOCUMENTS

| | | |
|---|---|---|
| 4,535,154 | 8/1985 | Keefer et al. . |
| 4,954,526 | 9/1990 | Keefer . |
| 5,028,627 | 7/1991 | Kilbourn et al. . |
| 5,039,705 | 8/1991 | Keefer et al. . |
| 5,059,712 | 10/1991 | Griffith . |
| 5,132,453 | 7/1992 | Griffith . |
| 5,155,137 | 10/1992 | Keefer et al. . |
| 5,158,883 | 10/1992 | Griffith . |
| 5,185,376 | 2/1993 | Diodati et al. . |
| 5,196,195 | 3/1993 | Griffith . |
| 5,198,428 | 3/1993 | Sivaramakrishnan et al. . |
| 5,208,233 | 5/1993 | Keefer et al. . |
| 5,212,204 | 5/1993 | Keefer et al. . |
| 5,216,025 | 6/1993 | Gross et al. . |
| 5,250,550 | 10/1993 | Keefer et al. . |

OTHER PUBLICATIONS

Medline 94188941 15 Mar. 1994.
Biosis 95:35515 1994.
by Carl Nathan, titled "Nitric oxide as a secretory product of mammalian cells", FASEB J. (1992) 6(12), 3051–64.
by Feldman, Griffith, Stuehr, titled "The surprising life of nitric oxide", Chem. Eng. News (1993)71(51),26–38.
by Merritt, titled "Nitric Oxide: An Important Bioregulator", Transplation Proceedings, (1993), 25(2),2014–2016.
by Moncada, Palmer, Higgs, titled "Nitric Oxide: Physiology Pathophysiology, and Pharmacology", Pharmacol. Rev. (1991).
by Lowenstein, Dinerman, Snyder, titled "Nitric Oxide: A Physiologic Messenger", Ann. Inter. Med.,(1994), 120(3).
by Berdeaux, titled "Nitric Oxide: An Ubiquitous Messenger", Fundam. Clin. Pharmacol. (1993), 7, 401–11.
by Hibbs, Vavrin, Taintor, titled "L–Arginine is Required for Expression of the Activated Macrophage Effector Mechanism Causing Selective Metabolic Inhibition in Target Cells", J. Immunol. (1987), 138(2), 550–65.
by Hibbs, Taintor, Vavrin, Rachlin, titled "Nitric Oxide: A Cytotoxic Activated Macrophage Effector Molecule", Boichem. Biophys. Res. commun. (1988), 157(1), 87–94.
by Buster, Powell, Miller, Ramirez, Summersgill, titled "Role of Nitric Oxide in Killing of Legionella Pneomophila in Gamma Interferon–Activated Macrophages", Legionella (1993), 109–11.

by Adams, Hibbs, Taintor, Krahenbuhl, titled "Microbiostatic Effect of Murine–Activated Macrophages for Toxoplasma Gondii. Role for Synthesis of Inorganic Nitrogen Oxides from L–arginine", J. Immunol. (1990), 144(7),2725–9.
by Tamir, Lewis, Walker, Deen, Wishnok, Tannenbaum, titled "The Influence of Delivery Rate on the Chemistry and Biological Effects of Nitric Oxide", Chem. Res. Toxicol. (1993), 6(6),895–9.
by Morley, Maragos, Zhang, Boignan, Wink, Keefer, titled "Mechanism of Vascular Relaxation Induced by the Nitric Oxide (NO)/Nucleophile Complexes, a New Class of Nitric Oxide–Based Vasodilators", J. Cardiovasc. Pharmacol. (1993).
by Baum, titled "Complexes Control Nitric Oxide Release", Chem. & Engr. News, Sep. 14, 1992, 32–33.
by Maragos, Morley, Wink, Dunams, Saavedra, Hoffman, Bove, Isaac, Hrabie, Keefer, titled "Complexes of NO with Nucleophiles as Agents for the Controlled Biological Release of Nitric Oxide", J. Med. Chem. (1991).
by Hrabic, Klose, Wink, Keefer, titled "New Nitric Oxide–Releasing Zwitterions Derived from Polyamines", J. Org. Chem. (1993), 58(6), 1472–6.
by Diodati Quyyumi, Keefer, titled "Complexes of Nitric Oxide with Nucleophiles as Agents for the Controlled Biological Release of Nitric Oxide: Hemodynamic Effect in the Rabbit", J. Cardiovasc. Pharmacol. (1993), 22(2), 287–92.
by Maragos, Wang, Hrabie, Oppenheim, Keefer, titled "Nitric Oxide/Nucleophile Complexes Inhibit the In Vitro Proliferation of A375 Melanoma Cells Via Nitric Oxide Release", Cancer Res. (1993), 53(3), 564–8.
by Drago, Karstetter, titled "The Reaction of Nitrogen (II) Oxide with Various Primary and Secondary Amines", J. Am. Chem. Soc., (1961), 83, 1819–22.
by Braman, Hendrix, titled "Nanogram Nitrite and Nitrate Determination in Environmental and Biological Materials by Vanadium(III) Reduction with Chemiluminescence Detection", Anal. Chem. (1989) 61(24), 2715–18.
by Smith, Dunphy, Strang, Marletta, titled "The Influence of Wound Healing on Urinary Nitrate Levels in Rats", Wounds, (1991), 3(1), 50–8.
by Bulgrin, Shabani, Smith, titled "Arginine–Free Diet Suppresses Nitric Oxide Production in Wounds", J. Nutr. Biochem. (1993), 4(10), 588–93.

*Primary Examiner*—Paul J. Killos
*Attorney, Agent, or Firm*—Renner, Kenner, Greive, Bobak, Taylor & Weber

[57] ABSTRACT

The invention describes water insoluble polymeric NON-Oate complexes which are capable of accelerating wound repair through the controlled therapeutic release of NO. The composition is additionally indicated to be capable of containing an absorbent material, optionally with a matrix material included.

20 Claims, 4 Drawing Sheets

POLYMERIC WOUND HEALING ACCELERATORS

TECHNICAL FIELD

The invention described herein pertains generally to water insoluble polymeric NONOate complexes which are capable of accelerating wound repair through the controlled therapeutic release of NO.

BACKGROUND OF THE INVENTION

Recent research has shown that nitric oxide (NO) is a vital biological molecule. NO plays a central role in such diverse processes as host defense, cardiovascular regulation, signal transduction, neurotransmission and wound healing. The enzyme nitric oxide synthase (NOS) converts L-arginine into L-citrulline and NO, and numerous cells involved in the wound healing process have shown NOS activity. The exact functions of NO in tissue repair have not been established, although a likely major role of NO is that of a cytotoxic or cytostatic agent released by macrophages and other phagocytic cells during the early inflammatory phase. NO released from wound resident cells may also be important in unique cell signalling pathways and the re-establishment of the microcirculation as newly vascularized tissue is formed.

Oxidation of NO produces unstable intermediates (such as $N_2O_3$ and $N_2O_4$) and subsequently the stable metabolic products nitrite ($NO_2$) and nitrate ($NO_3$). Previous studies have shown that urinary $NO_2$ is negligible in wounded or infected rats and that urinary $NO_3$ is an accurate indirect measure of NO production.

Previous work has shown that urinary $NO_3$ levels in normal excisionally wounded rats rises sharply upon wounding and remains significantly elevated over the course of tissue repair for up to 18 days following external wound closure. However, two common impaired wound models, steroid-treated rats and experimentally induced diabetic rats, both showed suppressed NO synthesis during wound repair. This suggests that the metabolism of NO by functional biological cells may be critically important during tissue repair. Furthermore, topical application of the NOS inhibitors $N^G$-monomethyl-L-arginine (LMMA) and $N^G$-nitro-L-arginine (LNA) significantly reduced NO synthesis ($P<0.05$) in wounds of normal rats, demonstrating that topical application of therapeutics can alter normal NO metabolism. If insufficient NO synthesis at the wound site is a key factor in impaired wound healing, then controlled topical delivery of NO to the local wound environment may be a new therapy for accelerating the healing of both chronic and normal wounds. Topical NO delivery may also be a crucial component of a new generation of wound dressings, since few controlled release drugs are currently available.

Recently, complexes formed by reacting nitric oxide with certain nucleophiles have been introduced as a new class of NO-releasing compounds. Keefer and coworkers have synthesized zwitterionic polyamine/NO adducts referred to as NONOates. In U.S. Pat. No. 5,250,550, Keefer et al. shows the following nitric oxide-polyamine complexes with pharmaceutically acceptable salts thereof as useful cardiovascular agents:

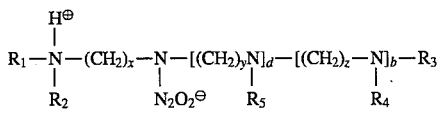

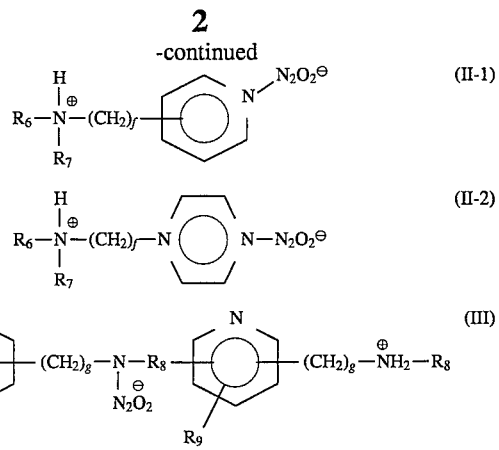

Alternatively, U.S. Pat. No. 5,212,204 to Keefer et al., describes antihypertensive compositions and a method of lowering blood pressure in mammals, wherein the active component of the composition is a compound of the following formula (IV)

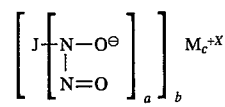

wherein J is an organic or inorganic moiety and $M^{+x}$ is a pharmaceutically acceptable cation which does not render the compound unstable or insoluble in water.

Previous Keefer patents, e.g., U.S. Pat. No. 5,208,233 also discussed anti-hypertensive compositions and methods of lowering blood pressure in mammals, can be characterized as shown in the following formula (V)

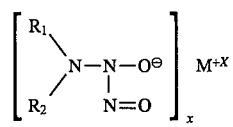

wherein an ionic-type association was shown, and wherein when $R_1$ and $R_2$ were bonded together, the following groups (VI-1 through VI-4) were preferred:

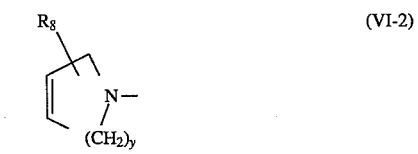

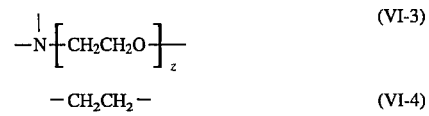

Additional uses for NO were shown in U.S. Pat. No. 5,185,376 wherein platelet aggregation inhibition in vivo was shown with physiologically compatible compounds containing at least one N-oxo-N-nitrosoamine moiety in a molecule thereof, wherein the physiologically compatible compound released nitric oxide in a sustained and controllable fashion in vivo. The types of compounds listed for this application were DEANO (VII)

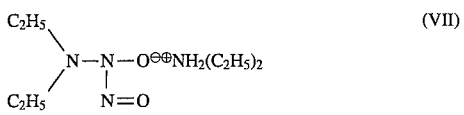

and the nitric oxide addition product of the polyamine spermine (VIII);

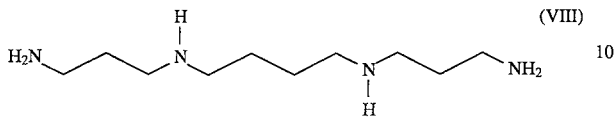

NIPRIDE (nitroprusside), formula (IX);

and ASA (aspirin), formula (X).

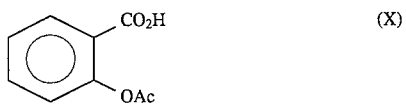

These NONOates release quantitative amounts of NO in aqueous media, and the rate and extent of NO generation appear to depend on pH, temperature, and the identity of the nucleophile residue NONOate compounds can be used as NO-based vasodilators, and may have other clinical applications, such as anti-tumor therapy. However, delivery of NO to wounds via these soluble amine-based NONOates is complicated by the solubility of toxic amines that remain after NO is released.

This invention involves polymer/NO adducts that are insoluble, non-toxic, and exhibit a long, controlled release of NO in aqueous solution to create a new class of NONOates. The polymeric NONOate, NO-polyethyleneimine cellulose (PEIC-NO), releases a significant amount of NO over a long period of time in an aqueous environment. PEIC-NO was chosen for wound healing studies due to its low toxicity, ease of application, and relatively long half life (approximately 960 min). Furthermore, another cellulose derivative, carboxymethyl cellulose, is a major component of most existing hydrocolloid wound dressings, and therefore incorporation of PEIC-NO into commercially available dressing formulations should be feasible.

SUMMARY OF THE INVENTION

In accordance with the present invention, there is provided a topical delivery system of NO in a controlled release manner.

It is an object of this invention to provide a topical delivery system for NO using a polymeric carrier.

It is another object of this invention to use controlled release NO applied topically to a wound to promote wound repair.

It is still another object of this invention to use a polymeric absorbant dressing material which is derivatized with NO which when topically applied will release therapeutic amounts of NO to the wound.

It is yet another object of this invention to use an insoluble NONOate complex which releases therapeutic amounts of NO to the wound in contrast to soluble NONOate complexes which can migrate away from the surface of the wound, and potentially cause detrimental systemic effects.

It is still yet another object of this invention to use PEI cellulose NONOate as the insoluble polymeric NO delivery system.

These and other objects of this invention will be evident when viewed in light of the drawings, detailed description, and appended claims.

BRIEF DESCRIPTION OF THE DRAWINGS

The invention may take physical form in certain parts and arrangements of parts, a preferred embodiment of which will be described in detail in the specification and illustrated in the accompanying drawings which form a part hereof, and wherein.

DETAILED DESCRIPTION OF THE INVENTION

Figure 1:
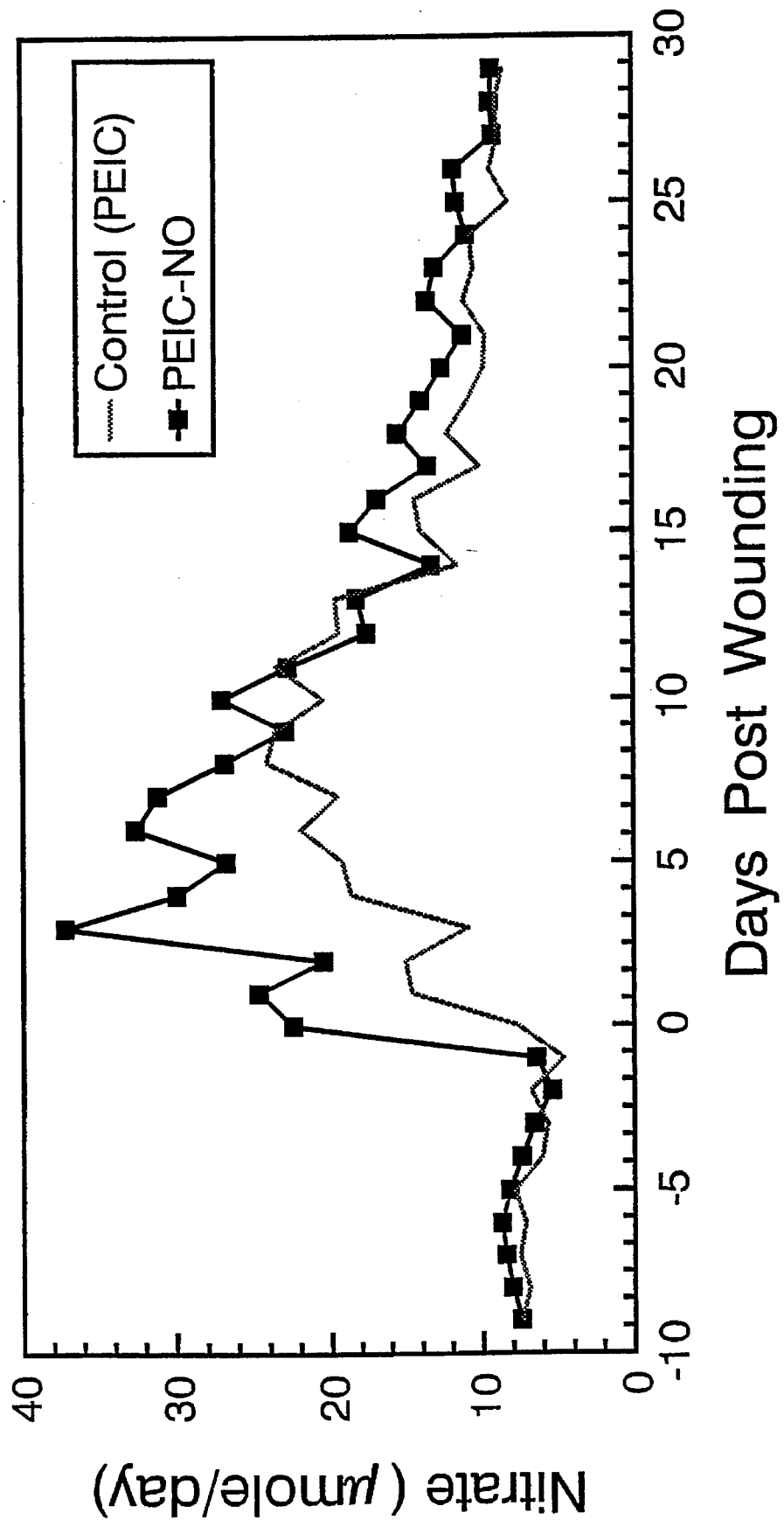
FIG. 1 is plot of urinary nitrate output per day in rats comparing a control (PEIC applied topically to a wound) and a sample (PEIC-NO applied topically to a wound) showing the increased urinary nitrate output for the NO treated wound.

Referring now to the drawings wherein the showings are for purposes of illustrating the preferred embodiment of the invention only and not for purposes of limiting the same, the Figures show a the ability of polymeric NONOates which when topically applied with release therapeutic amounts of NO which accelerates wound healing.

The best mode for carrying out the invention will now be described for the purposes of illustrating the best mode known to the applicant at the time. The examples are illustrative only and not meant to limit the invention, as measured by the scope and spirit of the claims.

EXAMPLES

Materials:
Polyethyleneimine cellulose (PEt-cellulose) was purchased from Sigma Chemical Company (St. Louis, Mo.) (fine or medium mesh anion exchange resin). Potassium nitrate (99.999%), and acetonitrile (99.5%) were purchased from Aldrich Chemical Company (Milwaukee, Wis.). Arginine modified (2%), AIN-76 low nitrate diet was purchased from ICN Biochemicals (Cleveland, Ohio). Vanadium III Chloride (99%) was purchased from Johnson Matthey/Alfa Products (Ward Hill, Mass.). Dense silicone rubber foam was provided by VariSeal Corporation (Parkman, Ohio). Sterile Bioclusive (TM) transparent dressing was purchased from Johnson & Johnson Medical Inc. (Arlington, Tex.). Water for solution prepration and rat consumption was purified with a Milli-Q (TM) cartridge filtration system (Millipore Corporation, Bedford, Mass.). Nitric oxide was purchased from Matheson Products, Inc. (Twinsburg, Ohio). Other reagent grade materials were purchased from Fisher Scientific (Pittsburgh, Pa.).
Experimental Method:

All procedures for animal experimentation were approved by the University of Akron Animal Care Committee. Male Sprague Dawley rats (75–99 g) were purchased from Zivic Miller Co. (Zelienople, Pa.). The animal storage facility provided alternating 12 hour light/dark cycles with constant humidity (50–60%), and temperature (21°–25° C.). Rats were quarantined for two weeks upon arrival, then transferred to another room and acclimatized for another 7 days. Rats were provided clean bedded cages, given distilled, deionized water ad libitum, and fed a custom low nitrate ($NO_3$) diet containing 2% arginine. Rats were transferred to metabolic cages and randomly assigned to either a control (n=6) or a treatment (n=9) group.

Urine was collected at 24-hour intervals for 9 days prior to wounding to establish baseline urinary nitrate output levels. Bacterial growth was inhibited by adding 5 ml of 3 mol/L HCl to each urine collection vial, which maintained urine at or below pH 1. The low urinary pH also helped to maintain optimal NO analyzer performance during nitrate analysis. Urine was also collected at 24-hour intervals throughout the course of the wound healing. Samples were used immediately or kept frozen until analyzed.

On the day of wounding, urine was collected and rats were anesthetized with Nembutal (40 mg/Kg i.p.). The dorsal side of each rat was shaved and then cleaned with a sterile, isopropanol soaked pad. Using sterile instruments and aseptic technique, each rat received a 2 cm×2 cm square, full thickness wound by removing the dermis and panniculus carnosus. A silicone rubber foam backed with a medical grade adhesive and with a 4 cm×4 cm square hole was placed on the skin adjacent to the wound to hold the treatment compound and to prevent wound contamination. The silicone wells also prevented skin contraction at the wound edge typically seen during early post wound healing in rodents. After applying the wound treatment, the silicone wells were covered with Bioclusive film and then Vetrap.

Treated rats received 200 mg of NONOate (PEIC-NO) and 200 uL of sterile 1X PBS. Control rats received 200 mg of PEIC and 200 uL of sterile 1X PBS. Rats were also injected with gentamicin (4.4 mg/Kg i.m.) while under anesthesia. After surgery and wound imaging, each rat was placed on an isothermal pad and monitored closely until it recovered from anesthesia, then returned to its metabolic cage. The treatment and control topical applications were previously coded to provide a blinded study throughout the course of experiment.

PEI-Cellulose NONOate Synthesis:

In a slight modification of the high pressure technique developed by Drago and Karstetter, PEI Cellulose (7.0 g, 15.4 mmol) with 70 ml acetonitrile was placed in a modified Ace thread reaction bottle equipped with a magnetic stir bar. The solution was charged with nitrogen gas for 10 minutes through a 4-way gas valve setup that consisted of two gas inlets for NO and $N_2$ that could be delivered simultaneously, a third outlet was used to keep the system open. All gas connections were made with transparent Teflon tubes (0.25 in OD) and stainless steel swagelock fittings. Nitric oxide gas was then administered at a pressure of 70 psig for 30 minutes and the reaction bottle was closed, keeping the reaction under pressure. This procedure for administering NO gas was repeated every other day for 10 days after which the excess NO was vented and $N_2$ gas was administered for 15 minutes. The yellow product (6.82 g) was isolated by filtration, washed with acetonitrile and then with ether, and dried in vacuo overnight. The polyethyleneimine cellulose polymer relased approximately 67 nmoles of NO/mg of polymer in a pH 7.4 buffer.

The resulting product is shown in diagrammatical form (XI) below.

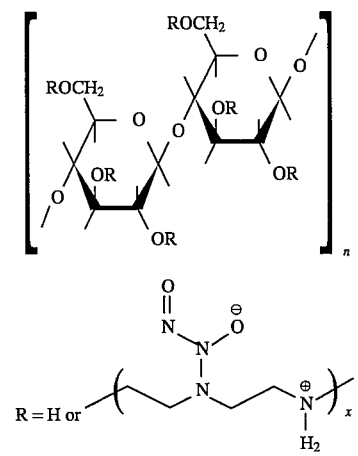

ED-BDE NONOate Synthesis:

A crosslinked poly(ethylene diamine-co-1,4-butanediglycidyl ether) was prepared by reacting approximately equimolar amounts of ethylene diamine and 1,4-butanediglycidyl ether) resulting in a brittle polymer. Approximately 150 ml of distilled water was added and the polymer allowed to swell, followed by filtering and washing with acetone. The polymer was oven dried at 50° C. The value of x is dependent upon the initial quantities of reactants polymerized.

To approximately 0.5 g of polymer in 25 mL acetonitrile, NO gas was added at 70 psi for 25 minutes. The valve to the reaction vessel was closed and the reaction proceeded for 48 hours. The reactor was vented and purged with nitrogen and additional NO added for 30 minutes at 70 psi. After closing the reactor valve, the reaction was allowed to proceed for an additional 24 hours. The final product was filtered and washed with ether. The final NONOate polymer was a white solid powder which was insoluble in water. However, upon contact with water, the NONOate polymer released NO gas and regenerated the initial copolymer. The poly(ethylenediamine-co-1,4-butanediglycidyl ether) polymer released 65 nmoles of NO/mg polymer in pH 7.4 buffer.

The above reaction is shown diagrammatically below.

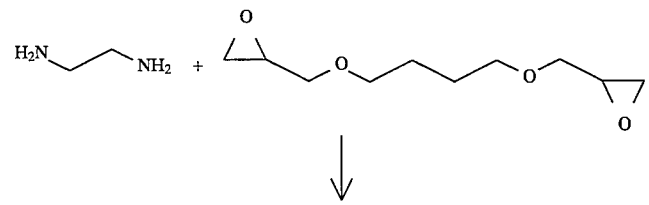

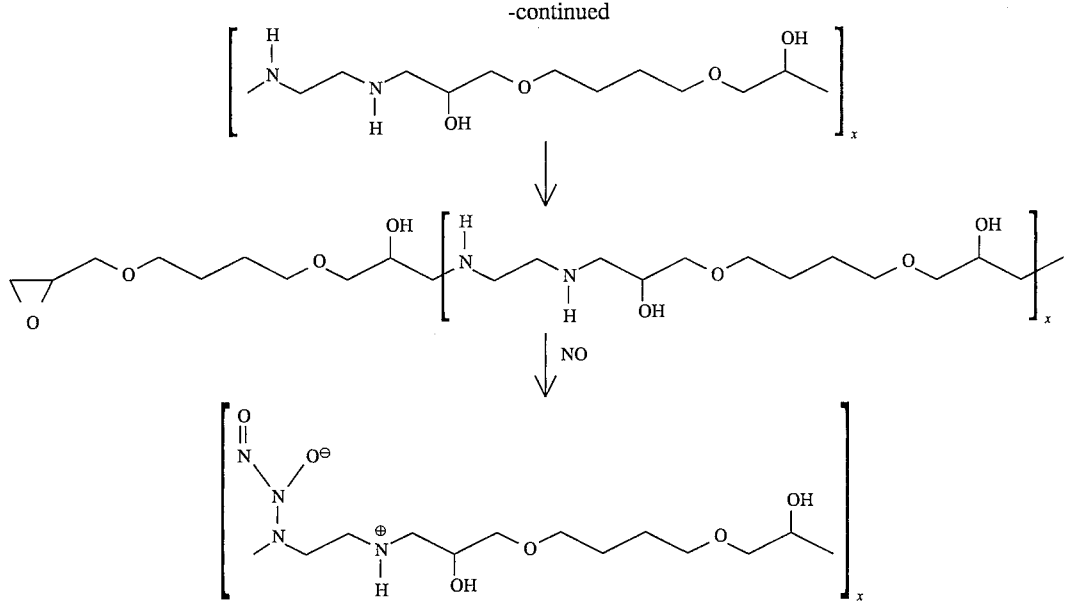

While two synthetic procedures are described above, there is no need to limit the application to the specific polymers discussed, although they represent the best mode known to the inventors to date. The use of other polymers, such as the use of a dextran substrate is also envisioned within the scope of this application. The discussion of this substrate is contained in copending application U.S. Ser. No. 08/065,742, which is fully incorporated by reference herein.

Video Image Analysis:

Immediately following wounding and every 3 days thereafter, each wound was videotaped using a video camera (Nikon VN-3000 with a micro-focousing 6X power zoom lens) and VHS tape (FUJI AN Master Super XG). After carefully cleaning each wound of any residue with sterile 1×PBS, a self-adhesive circular label (1.9 cm diamter) was placed adjacent to the wound. This served as an external standard during analysis of the video image and enabled the lens-to-wound distance to vary. The camera lens was positioned perpendicular to the wound site, with the wound and external standard in the same horizontal plane, and the lens was focused to give the largest possible image.

Digital computer analysis of wound images was accomplished by inputing the camera output signal into a spectrum NTSC+frame grabber board (Redlake Corporation, Morgan, Hill, Calif.) installed in a Gateway 2000 386/16SX computer (Gateway 2000, Inc. North Sioux City, S. Dak.). Using Accuware image analysis software (Automated Visual Inspection, Santa Clara, Calif.), several optimal images showing the wound and external standard were consecutively captured and displayed on a Samsung CSA7571 multiscanning 17 inch RGB monitor (Samsung Information Systems America, Inc.; San Jose, Calif.). The perimeter of the wound and external standard were traced with a mouse, and the pixel area of each image was computed. Relative wound areas were obtained by using the ratio of wound to external standard, giving measurements that were independent of camera-to-wound distance. Each relative wound area was expressed as a fraction of the original and plotted versus time to determine the wound healing progress. A paired two-tailed student's t-test was used to assess significant differences in wound healing between treated and control rats.

Nitrate Analysis:

All urine samples were assayed for nitrate ($NO_3$) using a Monitor Labs Model 8440 Nitrogen Oxides Analyzer (Lear-Siegler Corporation, Englewood, Colo.) and a modification of the method described by Braman and Hendrix. A custom impinger was filled with 40–50 ml of a reducing solution of Vanadium III Chloride ($VCl_3$, 0.4 mol/L) in 1.5 mol/L of HCl. The reducing solution was heated to 95°–100° C. and degassed with helium set at a flow rate of 125 mL/min. Urine samples were injected into the reducing solution through a teflon-lined septum, and the $VCl_3$ reduced any $NO_3$ present to NO. The helium flow carded newly generated NO through a second impinger filled with 1 mol/L NaOH to remove any acidic gases. The flow rate of the analyzer vacuum pump (i.e., the sample inlet flow) was set at 150 mL/min with a micrometering valve. A "T" connector between the analyzer inlet and the NAOH impinger provided an open system that maintained a steady input flow rate and avoided the problem of matching analyzer inlet and helium flow rates. The NO entering the analyzer and the subsequent chemiluminescent reaction (between $O_3$ generated by the analyzer and NO) determined the amount of NO per sample. Known concentrations of $KNO_3$ were also injected and used to determine daily standard curves, which were used to calculate the average $NO_3$ output (gmol/day) per animal. The output signal was captured by an HP3392A integrating recorder (Hewlett Packcard CO; Avondale, Pa.). Duplicate injections of all urine samples were run and the average values used as a daily $NO_3$ output for each animal. An unpaired two-tailed student's t-test was used to assess significant differences in urinary $NO_3$ concentration before and after wounding between treated and control rats.

NONOate Analysis:

The analysis of the PEIC-NO was performed on a Monitor Labs Model 8440 Nitrogen Oxide Analyzer (Lear-Siegler Corporation, Englewood, Colo.) connected to a LC/9540 chromatography data integrator (IBM, Inc., Danbury Conn.). The sampling chamber consisted of a gas impinger bottle modified with two way valves that allowed NO gas to accumulate in the chamber. One end of the sampling chamber was connected to the NO analyzer while the other end was connected to a flow meter and a helium gas tank. Helium gas was pumped through the system at 10 psig and the flow meter adjusted to 150–200 mL/min. The 150 mL sampling chamber was filled with 50 mL PBS pH 7.4 and the solution degassed for 15 minutes. A 10 mg sample of the PEIC-NO was added, valves were closed and periodic readings were taken by opening the valves and sweeping the NO produced to the detector via the helium gas.

Kinetic measurements were obtained by calculating the concentration of NO released from the PEIC-NO using a 100 µmol/L $KNO_3$ standard curve. A release profile was obtained by plotting the running sum of NO produced (nmoles) versus time (hours). From this graph, the concentration of NO at infinity was determined. The first order reaction rate was calculated by plotting ln $(Conc_f - Conc_t)$ versus time (hours), allowing the K value and half life of the polymer to be computed.

Blood Pressure Measurements:

Telemetry devices were previously implanted in spontaneously hypertensive (SHR) or Wistar-Kyoto (WKY) rats. Systolic blood pressure (SBP), diastolic blood pressure (DBP), mean arterial blood pressure (MAP), heart rate (HR), and locomotor activity (ACT) were measured continuously at 24-hour intervals, using the Dataquest IV Data Acquisition System (Data Sciences Inc., St. Paul, Minn.). The telemetry device was implanted by making a midline abdominal incision in anesthetized rats and inserting the flexible catheter tip of the radio transmitter into the descending aorta between the renal vessels and the iliac artery. The transmitter was placed in the peritoneal cavity and sutured to the abdominal wall as the midline incision was closed. Animals were placed in individual recovery cages for one week. A receiver was placed under each cage, which sent signals continuosly to a computerized data acquisition system in a separate room. Parameters were measured and saved between every 20 seconds to every 5 minutes, and then averaged in 30 minute intervals. Baseline blood pressure was recorded prior to wounding, at the time of wounding, and following topical application of NONOate or anesthetic injection (i.p.). Topical NONOate and a 3% solution of anesthetic sodium brevital (50 mg/Kg i.p.) were administered during a 3 day interval. Systolic blood pressure was recorded and averaged data obtained was plotted versus time to indicate any significant changes in blood pressure over time for both topical NONOate and Brevital injection. A paired two-tailed student's t-test was performed to assess significant differences in systolic blood pressure upon topical delivery (NONOate) or injected (brevital) rats.

Discussion

The urinary $NO_3$ profile, which indirectly measures NO release from wounds, is shown in FIG. 1. Day zero (0) is the day of wounding, and each data point represents the mean daily urinary $NO_3$ output for each group. The mean (n=9 days) pre-wound urinary $NO_3^-$ output was 6.7±0.34 S.E.M versus 7.4±0.37 S.E.M gmol/day $NO_3$ for control and NONOate groups respectively. There were no significant differences in urinary $NO_3^-$ output for both groups during pre-wounding.

In the early phase of healing (n=3 days, days 0–2), the mean urinary $NO_3^-$ output was 12.4±2.4 S.E.M and 22.5±1.1 S.E.M µmol/day $NO_3^-$ for control and NONOate groups respectively (P<0.019). On day three (3) the PEIC-NO group had a urinary $NO_3$ output 3.5 times greater than the corresponding control group. The mean urinary $NO_3^-$ output from days 4–10 (n=7 days), was 28.1±1.2 S.E.M and 21.0±0.81 S.E.M µmol/day $NO_3^-$ for PEIC-NO and control groups, respectively (P<0.0004).

However, in the early post-wound phase of healing (n=11 days, days 0–10), the mean urinary $NO_3^-$ output was 17.7±1.5 S.E.M versus 27.4±1.4 S.E.M µmol/day $NO_3^-$ for control and NONOate respectively, which was extremely significant (P<0.0002). The mean urinary $NO_3^-$ output in the later phase of healing (n=14 days, days 16–29), was 10.2±0.43 S.E.M and 12.3±0.61 S.E.M µmol/day $NO_3^-$ for control and NONOate groups respectively (P<0.011).

Urinary $NO_3^-$ output dropped progressively 11 days after wounding for both groups. Nevertheless, urinary $NO_3^-$ production for the NONOate group was 79% higher than baseline between days 16–25 (n=9 days, P<0.0001), when the external wound was approximately 93% closed on day 21.

Figure 2:
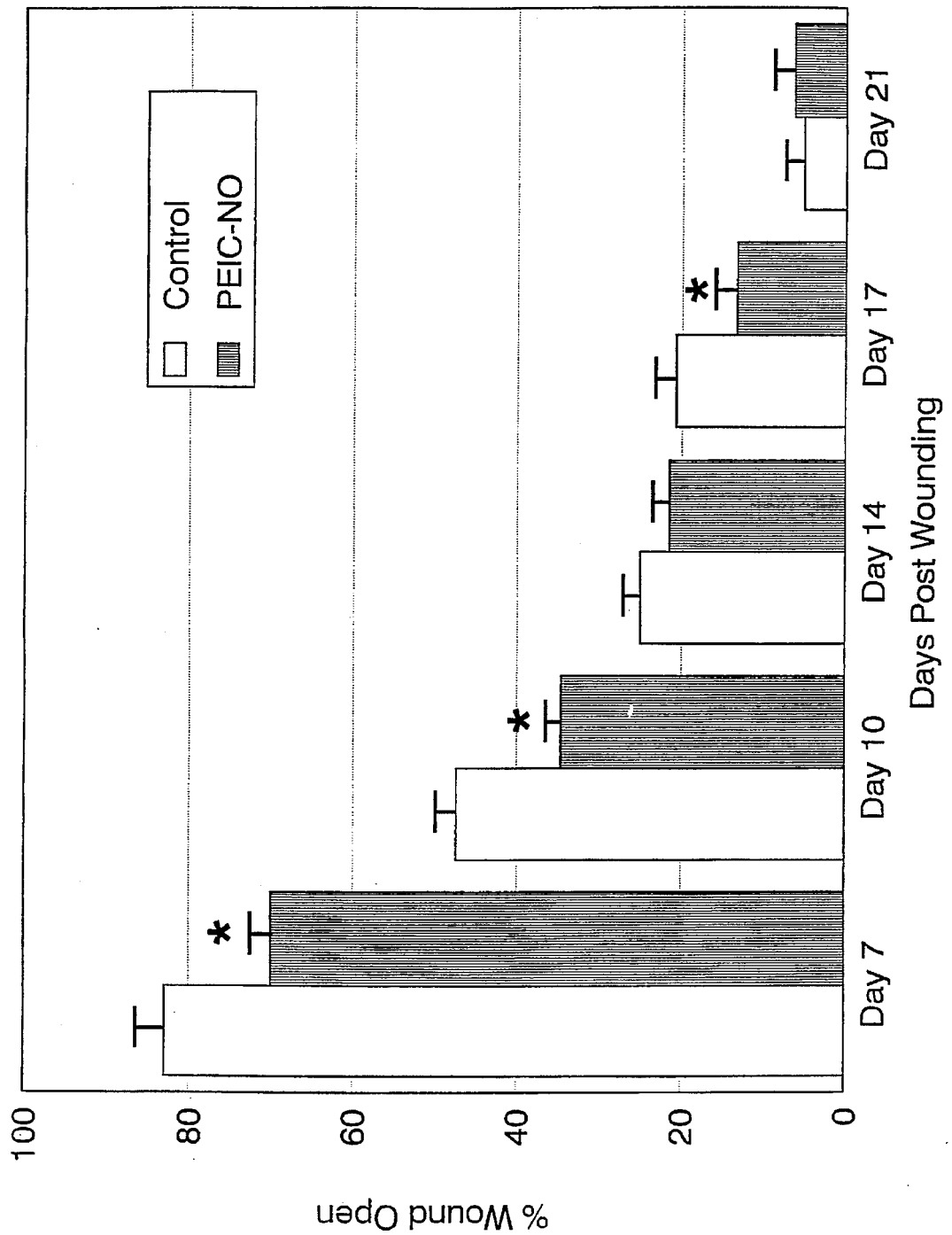
FIG. 2 is a plot of wound healing in rats comparing a control (PEIC applied topically to a wound) and a sample (PEIC-NO applied topically to a wound) showing differences in wound rate healing.
Figure 3:
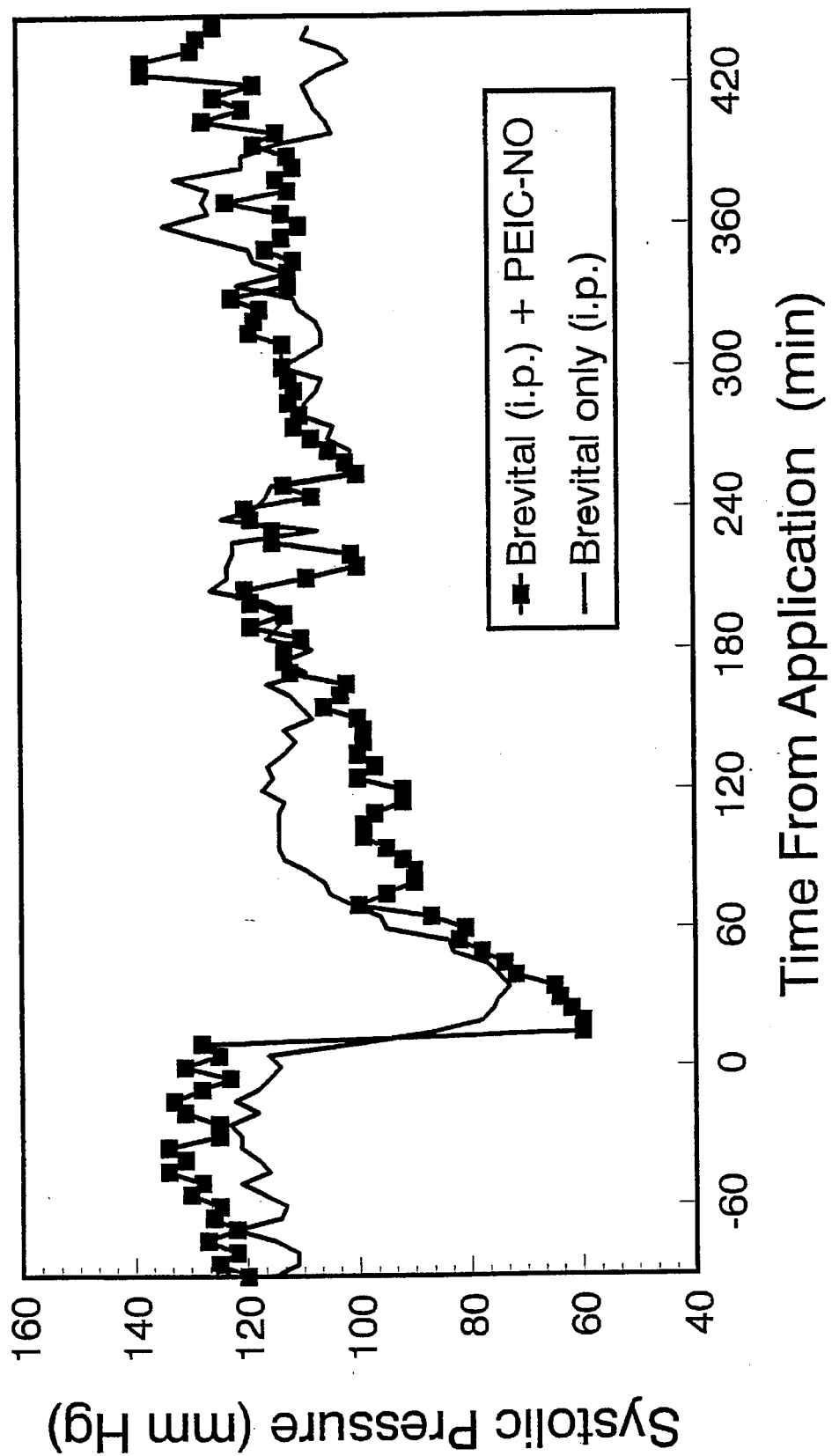
FIG. 3 is a plot of systolic pressure over time comparing a control (PEIC applied topically to a wound) and a sample (PEIC-NO applied topically to a wound)
Figure 4:
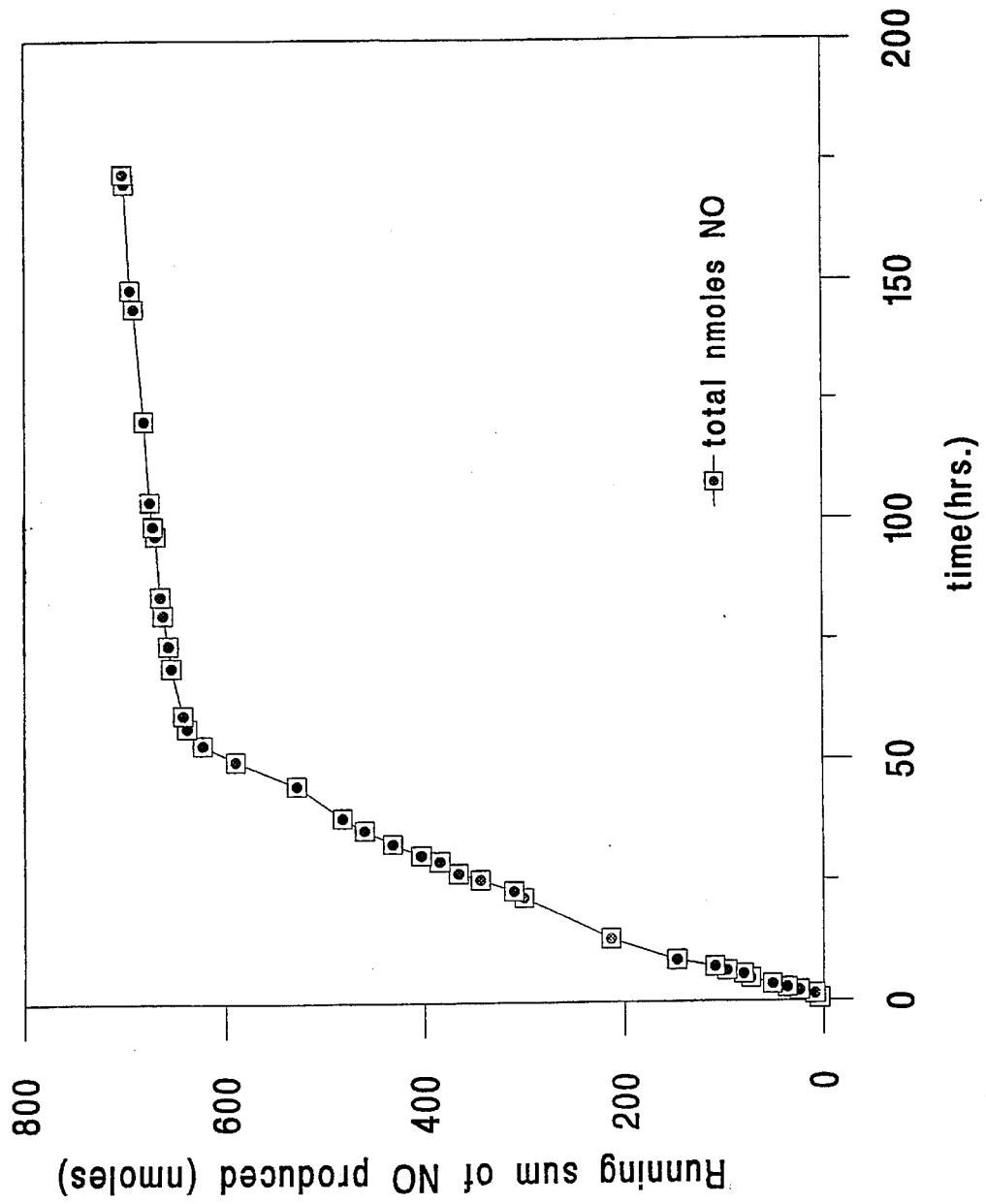
FIG. 4 is a release profile of PEIC-NO over time.

FIG. 2 shows wound healing data for both control and PEIC-NO treated rats. Based on percent wound open (relative to initial wound area), the healing of the PEIC-NO group wounds was significantly enhanced (P<0.05) on days 7, 10, and 17 relative to controls. FIG. 3 shows a typical systolic blood pressure profile arising from topical application of PEIC-NO. Systolic pressure dropped to 60 mmHg for approximately 45–50 minutes and then started to rise as the animals began recovering. About 3 hours after treatment, systolic pressure returned to normal levels. However, the initial drop in Systolic blood pressure was due mainly to the effect of the anesthetic breviatal, as seen by the close parallel between the PEIC-NO treated rat and the same rat given anesthetic alone. This indicates that the NONOate PEIC-NO has a short-lived hypotensive effect. FIG. 4 shows the NO release profile from polymeric PEIC-NO. The 10 mg sample of NO-PEIC released 685 nmoles of NO with a half life of 16 hours, which demonstrates NO-PEIC provides controlled NO release in physiological buffer over a prolonged period of time.

Polymeric NONOates used in the wound healing studies have the following desired properties: (1) they are stable solids; (2) are water insoluble; (3) yield NO without redox activation; (4) are kinetically well-behaved ($1^{st}$ order NO release); and (5) can be formulated into various physical structures. It may be possible to use in these wound studies NONOates which are water soluble but are encapsulated in polymeric devices or liposomes. The main concern is that the NONOate remain at the wound site and not migrate away to potentially give systemic side effects. The soluble NONOate may also be affixed to a polymer support via ionic interactions, for example, (since the NONOates are formed from poly cationic polyamines) they could be complexed with polyanionic resins.

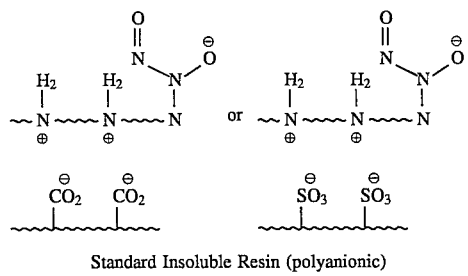

Standard Insoluble Resin (polyanionic)

This interaction could retain the NO donor at the wound site similar to that observed by polymeric NONOate.

Soluble NONOates could also be encapsulated into common materials used in wound dressings. For example, soluble solid NONOates could be mixed into urethane polymers. These polymers could be cast onto films or formed to produce a dressing. All that is required to release NO onto a wound is a source of $H^+$ (via partial hydration of the urethane) and a simple pathway for NO migration. Therefore, it is possible to trap the NO donor and still achieve localized NO release.

Aside from NONOates other NO donors are envisioned. S-nitroso-compounds could be used for example. For example S-nitroso-N-acetylpenicillamine (SNAP) releases NO under biological conditions. This material could be incorporated into a polymer or encapsulated in a control release system which would allow NO release at the wound site without migration away causing systemic effects. Proteins such as S-nitrosoalbumen could be used to deliver NO.

Other NO donors require some type of biological oxidation or reduction before NO can be formed. Compounds such as nitroglycerin (requires reduction) if affixed to a polymer or encapsulated and satisfactorily reduced could provide NO to a wound. Others like SIN-I (molsidomine) require oxidation from oxygen to release NO. Again polymers of molsidomine analogs could be envisioned under appropriate conditions, to deliver NO to a wound.

What has been shown is the ability to promote healing for all lesions, including all erupting ulcerations in the skin through the controlled release of topically applied NO polymeric complexes. This is accomplished through the fact that the NONOate is insoluble in an aqueous environment in contrast to prior art NONOate complexes which were soluble. The benefit of the incorporation of the nitric oxide into a polymeric matrix is that the shelf life of the complex is dramatically increased over that of prior art products, which tended to decompose immediately if not used, i.e., possessing no shelf life.

Another benefit of the polymeric complex carrier is that after the consumption or use of the nitric oxide substituent in the complex, the polymer which is left is biocompatible, unlike the amine complexes taught by the prior art.

The polymeric complex carrier may however, additionally include other materials, such as dressings. Various classes of dressings are currently used in the management of acute and chronic dermal wounds. Of these, the hydrocolloid dressings (HCD) dressings are used most frequently in the clinical setting. The high absorptive capacity characteristic of these dressings coupled with the occlusive and moist environment they provide lead to rapid granulation, re-epithelialization and wound closure.

Clinical applications for HCD dressings include the treatment of burns and burn donor sites, chronic venous ulcers, decubitus ulcers, leprous ulcers, epidermolysis bullosa, scleroderma, psoriasis and non-infected partial thickness wounds.

Conventional HCD dressings incorporate an adhesive mixture, usually composed of low and high molecular weight polyisobutylene, and absorbents such as gelatin, pectin and carboxymethyl cellulose, silica and cotton fibers. Representative HCD dressings are described, for example, in U.S. Pat. Nos. 3,972,328 (Aug. 3, 1976) to Chen, et al, 4,253,460 (Mar. 3, 1981) to Chen, et al, and 4,538,603 (Sep. 3, 1985) to Pawelchak, et al.

Various absorbents are currently used in the formulation of wound fillers and dressings. The key feature of these absorbents in their choice as wound dressing components appears to be their fluid handling capacity; biodegradability has not been an issue of major concern. In view of this, it is not surprising that recent histological studies show that the use of certain wound dressings lead to extensive non-resolved and deepseated chronic inflammation in externally healed tissue. Such inflammation can potentially be reduced by using dressing components that degrade to non-toxic and non-inflammatory products under physiological conditions.

In this context it should be noted that none of the commonly used biodegradable microspheres in controlled drug delivery (such as polylactides or gylcollides) possess any appreciable absorptive or fluid handling capacity.

The absorbents which are useful would include polymer compositions which are water swellable, water insoluble, hydrolytically labile and pharmaceutically acceptable crosslinked polysaccharide (preferably dextran) polymer compositions in the form of beads or microparticles. The microparticles are essentially spherical in shape and so may be referred to as microspheres. The product when dry is a free-flowing powder. The crosslinking groups are linear imidocarbonate groups, linear carbonate groups or a mixture thereof. The products are water insoluble at 25° C. and are degradable to a water soluble non-crosslinked polysaccharide in an essentially neutral aqueous medium at a temperature of at least 37° C. Because the products are degradable in essentially neutral aqueous media, they may be characterized as hydrolytically labile (or hydrolytically degradable). Hydrolytic lability also indicates that the products are biodegradable, i.e., capable of decomposition into water soluble products in the presence of aqueous body fluids such as blood and lymph at normal body temperature (37° C.). Microspheres are formed by crosslinking of a water-soluble non-crosslinked polysaccharide with a cyanogen halide under alkaline conditions under which crosslinking occurs, in the aqueous phase of a water-in-oil dispersion. The preferred cyanogen halide is cyanogen bromide. The crosslinked product comprises polysaccharide chains and crosslinking groups formed by the reaction with cyanogen halide and base. The crosslinking groups as formed are believed to be linear imidocarbonate groups which are bonded to different polysaccharide chains (or to distant parts of the same chain) through hydroxyl groups on the polysaccharide chains. These linear imidocarbonate groups may be partially hydrolyzed in acid to linear carbonate groups during workup.

The crosslinked product is essentially free of crosslinking groups other than those introduced through reaction with cyanogen halide and base. In particular, the crosslinked product is free of non-hydrolytically degradable crosslinking groups.

The starting polysaccharide is water soluble and may have a molecular weight from about 40,000 to about 1,000,000 or more. Preferably the starting polysaccharide has a molecular weight (average) from about 100,000 to about 1,000,000, more preferably from about 200,000 to about 600,000. The preferred starting polysaccharide is dextran.

The microparticles are essentially spherical in shape and are predominantly in the range of about 1 to about 100 microns. Generally the microparticles are predominantly in the range of about 2 to about 50 microns in diameter. The final product microspheres are in the form of a free-flowing powder.

It is essential to carry out the activation reaction in the aqueous phase of a water-in-oil dispersion in order to obtain spherical microparticles in the size ranges defined above. If water (without any oil phase) is used as the reaction medium a gel is initially formed. This gel must be broken up (e.g., in a blender) in the present of a dehydrating solvent such as ethanol in order to obtain a useful product. The final product of such processing is not in the form of spheres but rather is in the form of irregularly shaped aggregates.

The products being in the form of microspheres, offer several advantages over products in the form of aggregates. First, processing and formulation are easier. Second, the product is more uniform. As a consequence, products of this invention exhibit more uniform and more predictable degrees of swelling, rates of swelling and rates of hydrolysis or degradation in the presence of moisture than would a product in the form of aggregates.

In one mode of the invention, the polymeric NONOates are chemically grafted onto the Dextran particles described above, although a chemical entrapment is also possible depending upon the synthetic method chosen. A wound dressing according to this invention may comprise, for example, a blend of crosslinked polysaccharide microspheres of this invention with a hydrophobic adhesive polymeric matrix material, which blend is applied to one side or surface of an inert waterproof backing sheet.

At times, a matrix material may be incorporated into the absorbent materials described previously. This may be an amorphous polymer (having a glass transition temperature but no melting point) which is hydrophobic, chemically inert, pharmaceutically acceptable, adhesive, and solid at body temperatures. To the latter end, the glass transition temperature should be at least slightly above normal body temperature, e.g., not lower than about 45° C.

Suitable matrix materials are known in the art. The matrix material is rubbery (i.e., elastomeric) and hydrophobic. Examples of suitable matrix materials include various grades of polyisobutylene styrene-butadiene rubber, and butyl rubber (a copolymer of isobutylene with a small amount of isoprene). A low molecular weight polyisobutylene (average M.W. about 10,000 to about 50,000) is typically a matrix component.

The invention has been described with reference to preferred and alternate embodiments. Obviously, modifications and alterations will occur to others upon the reading and understanding of the specification. It is intended to include all such modifications and alterations insofar as they come within the scope of the appended claims or the equivalents thereof.

What is claimed is:

1. A process for the accelerated healing of skin wounds which comprises the step of topically adding a water insoluble nitric oxide polymer adduct which releases therapeutic amounts of nitric oxide in an aqueous environment to a surface of the wound.

2. The process of claim 1 wherein the adduct is essentially non-toxic to to a living organism when delivered in therapeutic amounts.

3. The process of claim 2 wherein nitric oxide is delivered in therapeutic amounts over a period of at least three weeks.

4. The process of claim 3 wherein when essentially all of the nitric oxide is delivered, the insoluble polymer is biocompatable.

5. The process of claim 4 wherein the adduct has a half life of at least 960 minutes.

6. An adduct which when topically applied to a wound surface accelerates the healing thereof, which comprise:
   (a) a water-insoluble polymer; and
   (b) a chemically bonded amount of nitric oxide to the polymer which is capable of being released from the polymer upon exposure to an aqueous environment in therapeutic amounts.

7. The adduct of claim 6 wherein the polymer is biocompatible after the release of nitric oxide.

8. The adduct of claim 6 wherein the polymer is selected from the group consisting of polyethyleneimine cellulose and poly(ethylene diamine-co-1,4-butanediglycidyl ether).

9. The adduct of claim 7 which further comprises an absorbent dressing.

10. The adduct of claim 9 wherein the dressing is selected from the group consisting of low and high molecular weight polyisobutylene, gelatin, pectin, carboxymethyl cellulose, silica, cotton fibers and polymer compositions which are water swellable, water insoluble, hydrolytically labile and pharmaceutically acceptable crosslinked polysaccharides in the form of microparticles.

11. The adduct of claim 10 wherein the crosslinking groups are selected from the group consisting of linear imidocarbonate groups, linear carbonate groups and mixtures thereof.

12. The adduct of claim 11 wherein the polysaccharide has a molecular weight from 40,000 to 1,000,000.

13. The adduct of claim 12 wherein the polysaccharide has a molecular weight from 100,000 to 1,000,000.

14. The adduct of claim 13 wherein the polysaccharide has a molecular weight from 200,000 to 600,000.

15. The adduct of claim 14 wherein the polysaccharide is dextran.

16. The adduct of claim 9 which further comprises a matrix material.

17. The adduct of claim 16 wherein the matrix is a blend of crosslinked polysaccharides and a hydrophobic adhesive polymeric matrix.

18. The adduct of claim 17 wherein the matrix is an amorphous, hydrophobic, chemically inert, pharmaceutically acceptable, adhesive polymer, which is a solid at body temperatures.

19. The adduct of claim 18 wherein the glass transition temperature of the matrix is not lower than 45° C.

20. The adduct of claim 19 wherein the matrix is selected from the group consisting of polyisobutylene styrene-butadiene rubber, butyl rubber and low molecular weight polyisobutylene.

* * * * *